United States Patent [19]

Nelson

[11] 4,209,645
[45] Jun. 24, 1980

[54] 2-DECARBOXY-2-HYDROXYMETHYL PGF$_2\alpha$ ANALOGS

[75] Inventor: Norman A. Nelson, Galesburg, Mich.

[73] Assignee: The Upjohn Company, Kalamazoo, Mich.

[21] Appl. No.: 20,599

[22] Filed: Mar. 15, 1979

Related U.S. Application Data

[60] Continuation of Ser. No. 784,995, Apr. 6, 1977, which is a division of Ser. No. 647,369, Jan. 8, 1976, Pat. No. 4,032,576.

[51] Int. Cl.$^2$ ............................................ C07C 177/00
[52] U.S. Cl. .................................................... 568/670
[58] Field of Search ......................................... 568/670

[56] References Cited
PUBLICATIONS

Derwent Abstract, 42368x/23, Imperial Chem. Inds. Ltd., 26.05.76.

Derwent Abstract, 47634a/26, U.S. 4088–691, Upjohn Co., (09.05.78).
Derwent Abstract, 47633a/26, U.S. 4088–690, Upjohn, (09.05.78).
Chem. Abstr., 87.22553f, Fried, Josef, Gen. Offen., 2,640,487.

Primary Examiner—Paul J. Killos
Attorney, Agent, or Firm—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

1 Claim, No Drawings

2-DECARBOXY-2-HYDROXYMETHYL PGF$_2\alpha$ ANALOGS

The present application is a continuation application of Ser. No. 784,995, filed Apr. 6, 1977, now pending issuance as a U.S. Patent; which is a divisional application of Ser. No. 647,369, filed Jan. 8, 1976, now U.S. Pat. No. 4,032,576.

The present invention relates to prostaglandin analogs, for which the essential material constituting disclosure therefor is incorporated by reference here from U.S. Pat. No. 4,032,576.

I claim:

1. A prostaglandin analog of the formula

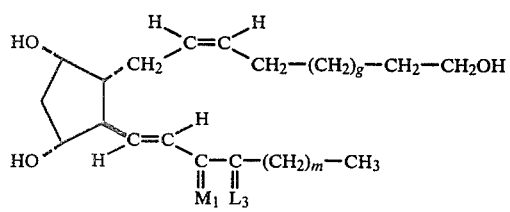

wherein M$_1$ is

or

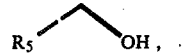

wherein R$_5$ is hydrogen or methyl;
wherein L$_3$ is

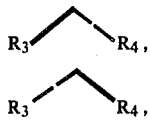

or a mixture of

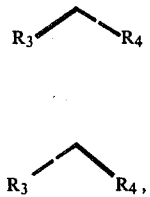

wherein one of R$_3$ and R$_4$ is fluoro and the other is hydrogen or fluoro;
wherein g is one, 2, or 3; and
wherein m is one to 5, inclusive.

* * * * *